United States Patent
Chang

(10) Patent No.: US 7,074,018 B2
(45) Date of Patent: Jul. 11, 2006

(54) DIRECT DRIVE LINEAR FLOW BLOOD PUMP

(76) Inventor: Sheldon Chang, P.O. Box 273, Port Jefferson, NY (US) 11777

( * ) Notice: Subject to any disclaimer, the term of this patent is extended or adjusted under 35 U.S.C. 154(b) by 388 days.

(21) Appl. No.: 10/617,403

(22) Filed: Jul. 10, 2003

(65) Prior Publication Data
US 2005/0008509 A1    Jan. 13, 2005

(51) Int. Cl.
*F04B 17/00*    (2006.01)
*F04B 35/04*    (2006.01)

(52) U.S. Cl. .............. 417/410.3; 418/48; 604/151; 417/356

(58) Field of Classification Search ........... 417/410.3, 417/356, 410.4; 418/48; 604/151
See application file for complete search history.

(56) References Cited

U.S. PATENT DOCUMENTS

| | | | |
|---|---|---|---|
| 1,892,217 A | 12/1932 | Moineau | |
| 3,479,960 A | 11/1969 | Cardoso | |
| 4,482,305 A | 11/1984 | Natkai et al. | |
| 4,802,827 A | 2/1989 | Fujiwara et al. | |
| 5,184,940 A * | 2/1993 | Fujiwara et al. | 417/356 |
| 5,407,337 A * | 4/1995 | Appleby | 418/166 |
| 5,588,812 A | 12/1996 | Taylor et al. | |
| 5,692,882 A | 12/1997 | Bozeman, Jr. et al. | |
| 5,707,218 A | 1/1998 | Maher et al. | |
| 5,779,460 A * | 7/1998 | Marz | 418/48 |
| 5,857,842 A * | 1/1999 | Sheehan | 417/420 |
| 6,227,820 B1 * | 5/2001 | Jarvik | 417/423.12 |
| 6,245,007 B1 * | 6/2001 | Bedingham et al. | 600/16 |
| 6,247,892 B1 * | 6/2001 | Kazatchkov et al. | 415/68 |
| 6,361,292 B1 | 3/2002 | Chang et al. | |
| 6,398,522 B1 * | 6/2002 | Skill | 417/410.3 |
| 6,527,521 B1 * | 3/2003 | Noda | 417/355 |
| 6,544,015 B1 * | 4/2003 | Kaechele | 418/48 |
| 6,595,743 B1 * | 7/2003 | Kazatchkov et al. | 415/171.1 |
| 6,881,045 B1 * | 4/2005 | Zitka et al. | 418/48 |
| 2005/0008510 A1 * | 1/2005 | Gerstenberg | 417/410.4 |

OTHER PUBLICATIONS

Catanese et al., "Outpatient Left Ventricular Assist Device Support: A Destination Rather Than a Bridge," Ann Thorac. Surg., 62:646-53, 1996.

* cited by examiner

*Primary Examiner*—William Rodriguez
(74) *Attorney, Agent, or Firm*—Hoffmann & Baron, LLP

(57) ABSTRACT

A ventricular assistive device (VAD) based on a progressive cavity pump includes a pump housing having an inlet and an outlet, a pump stator contained within the pump housing, a pump rotor rotatably disposed within the pump stator, a motor including a motor rotor contained within the pump housing and a direct drive means connected between the motor rotor and an axial shaft of the pump rotor for rotating the pump rotor. The motor rotates the motor rotor, which in turn rotates the pump rotor through the direct drive means. The rotation of the pump rotor within the pump stator forms a plurality of cavities that carry blood forward through the pump housing from the inlet to the outlet as the motor drives the direct drive means.

21 Claims, 3 Drawing Sheets

DIRECT DRIVE LINEAR FLOW BLOOD PUMP

FIELD OF THE INVENTION

The present invention relates generally to ventricular assistive devices for pumping blood, and more particularly to a linear flow blood pump having an improved direct drive in the form of a gear driven rotor.

BACKGROUND OF THE INVENTION

Ventricular assistive devices (VADs) are mechanical pumps that compensate for damaged or otherwise impaired hearts. They are used to restore normal hemodynamics and end-organ blood flow.

Early VADs closely emulated the pumping mechanism of the heart. Such devices provided a chamber which blood could be drawn into and then expelled out. In the Thermo Cardiosystems pump, blood was drawn in and pushed out by means of a pusher plate mechanism. (Catanese et al., "Outpatient Left Ventricular Assist Device Support: A Destination Rather Than A Bridge," Ann. Thoracic Surg., 62:646–53, 1996).

There are several problems with such devices. First, the only controllable quantity is the speed of the electric motor, which determines the number of pressure pulses per minute and the total volume of blood flow. Thus, it is difficult to tailor such devices for the needs of particular patients or particular circumstances. Second, the devices are inefficient, because the initial tendency of the pusher plate is to push the blood in all directions. Although the blood flow is eventually confined to only one direction by the action of the valves, it takes energy to actuate the output valve and to overcome the initially diffused motion.

A significant improvement in VADs is achieved by replacing impeller pumps with axial flow pumps, such as the Nimbus pump (U.S. Pat. No. 5,588,812). Instead of using a pusher plate, axial flow pumps generally use blades or fins attached to a pump rotor to propel blood axially along a cylindrical conduit. However, blood has substantial viscosity and tends to also move radially with the propelling blades or fins. At a rotational speed of several thousand revolutions per minute, the centrifugal force cannot be ignored. As the centrifugally moving blood impinges against the walls of the cylindrical conduit, there is not only a loss of energy but also damage to the blood cells.

Co-owned U.S. Pat. No. 6,361,292, the specification of which is incorporated herein by reference, discloses a ventricular assistive device based on a progressive cavity pump. A progressive cavity pump does not use blades or fins to propel the blood. Instead, the pump stator and rotor are designed so that, when combined, there are a series of cavities formed between the pump rotor and the stator wall. Blood is carried through the pump chamber in these cavities when the rotor rotates or the rotor and stator both rotate. The cavities progress on a straight line path through the pump, providing an unobstructed channel for blood flow and minimizing the risk of thrombus, i.e., blood clotting. Thus, the progressive cavity linear flow pump provides a more efficient mechanism for transporting blood that also reduces damage to the blood cells and reduces the risk of thrombus.

SUMMARY OF THE INVENTION

The present invention is an improvement over the linear flow blood pump (LFBP) disclosed in commonly owned U.S. Pat. No. 6,361,292. Briefly, the present invention utilizes a direct drive device for driving the pump rotor.

The present invention is an axial flow blood pump generally including a pump housing having an inlet and an outlet, a pump stator contained within the pump housing, a pump rotor rotatably disposed within the pump stator, a motor including a motor rotor contained within the pump housing and a direct drive means connected between the motor rotor and an axial shaft of the pump rotor for rotating the pump rotor. The motor rotates the motor rotor, which in turn rotates the pump rotor through the direct drive means. The rotation of the pump rotor within the pump stator forms a plurality of cavities that carry blood forward through the pump housing from the inlet to the outlet as the motor drives the drive element. Preferably, the cavities progress in a straight line path through the pump.

In a preferred embodiment, the direct drive means includes a pinion gear fixed to the axial shaft of the pump rotor and a drive element, or ring gear, connected to the motor rotor. The pinion gear includes a plurality of external teeth and the drive element, or ring gear, includes a gear plate having a plurality of internal teeth engaging the external teeth of the pinion gear. There are m*n external teeth on the rotar shaft pinion gear and m*(n+1) internal teeth on the drive element, wherein m and n are integers. In a preferred embodiment, n−1 so that there are twice as many internal teeth on the ring gear as there are external teeth on the pinion gear. In this manner, the pump rotor is driven twice as fast as the motor rotor.

The ring gear plate further defines one or more external openings which are used for allowing blood to flow through at both the inlet end and the outlet end of the linear flow blood pump. The external openings are preferably aligned with the open cavities formed between the pump stator and the pump rotor. Also, the ring gear plate is preferably engaged with the motor rotor by a key and slot arrangement.

Also in the preferred embodiment, the pump stator is connected to the motor rotor for rotation therewith and the motor further includes a motor stator for rotating the motor rotor. The motor stator has at least one pair of windings that are arranged on opposite sides of the motor stator and are connected in parallel to reduce unbalanced magnetic forces. The motor stator is contained between an inner pump housing wall and an outer pump housing wall. Additionally, the motor stator and the motor rotor preferably include longitudinally spaced segments and the motor rotor further preferably includes an outer sleeve for supporting the motor rotor segments. In this preferred embodiment, the drive element is connected to the outer sleeve.

The present invention further involves a method for pumping blood through an axial flow pump including an inlet and an outlet. The method includes the steps of directly rotating a pump rotor rotatably mounted within a pump stator, thereby forming a plurality of moving cavities between the pump rotor and the pump stator, and carrying blood from the inlet to the outlet via the moving cavities. The pump rotor is directly rotated by a direct drive means connected between a motor rotor and an axial shaft of the pump rotor. Again, the direct drive means preferably includes a pinion gear fixed to the axial shaft of the pump rotor and a drive element, for example a ring gear, connected to the motor rotor. The pinion gear includes a plurality of external teeth and the ring gear includes a plurality of internal teeth engaging the external teeth of the pinion gear.

Other objects and features of the present invention will become apparent from the following detailed description considered in conjunction with the accompanying drawings.

It is to be understood, however, that the drawings are designed as an illustration only and not as a definition of the limits of the invention.

DETAILED DESCRIPTION OF THE PREFERRED EMBODIMENTS

The invention herein is a ventricular assistive device based on a progressive cavity pump. A progressive cavity pump does not use blades or fins to propel the blood. Instead, the pump stator and rotor are designed so that, when combined, there is a progressive series of cavities formed between the pump rotor and the pump stator. Blood is carried through the pump chamber in these cavities when both the rotor and the stator rotate.

Figure 1:
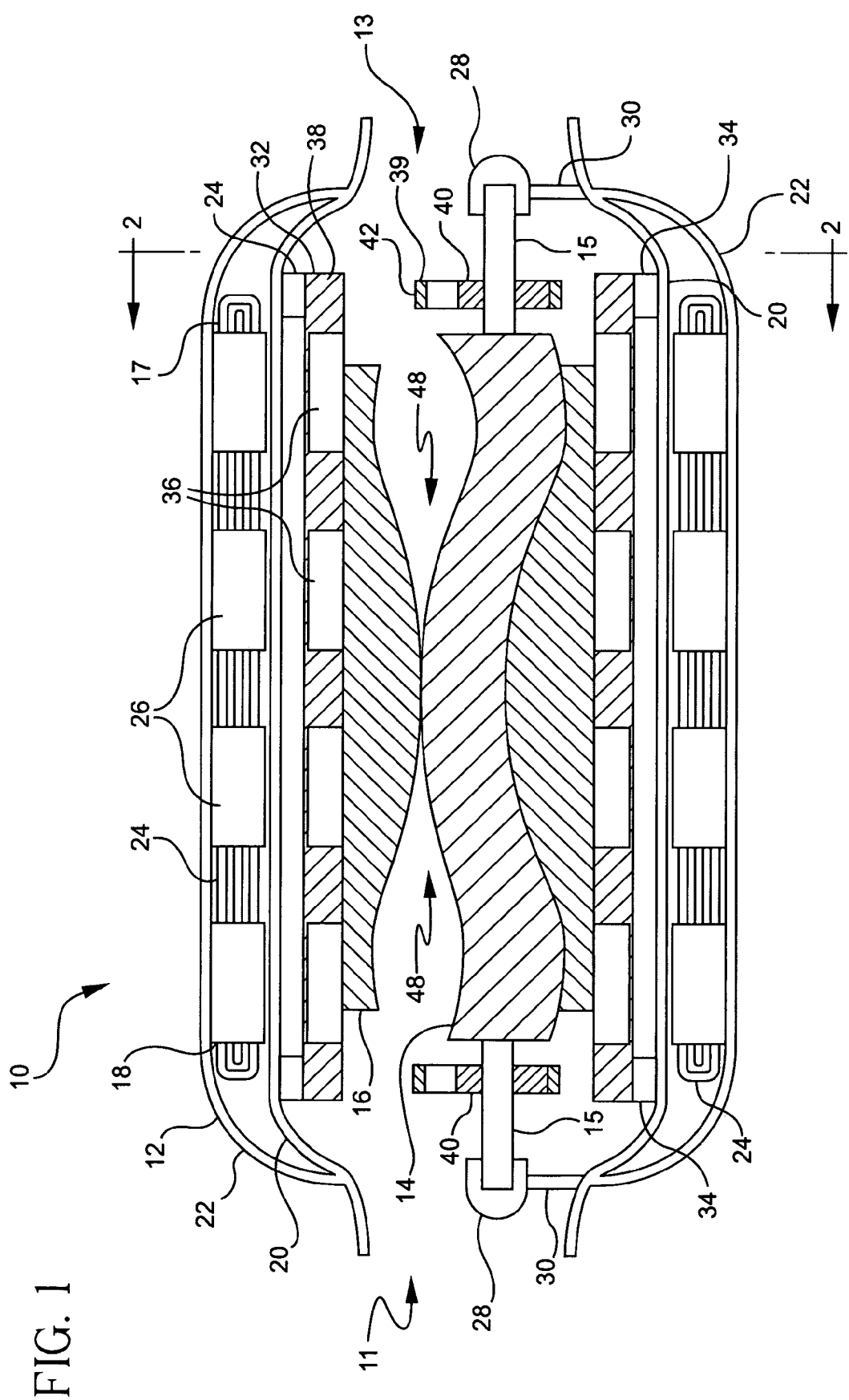
FIG. 1 shows a longitudinal cross-section view of the gear driven linear flow blood pump formed in accordance with the present invention.

Referring to FIG. 1, the pump 10 of the present invention generally includes a pump housing 12 defining an inlet 11 and an outlet 13 and having contained therein a pump rotor 14 and a pump stator 16. The pump rotor 14 is helical in shape, somewhat like a single-threaded screw, and preferably has a circular cross-section. The pump stator 16 resembles a double-threaded screw, closely engaged with the pump rotor 14.

In a preferred embodiment, a gear arrangement 39 drives the pump rotor 14 to rotate with the pump stator 16 in the same direction. The rotor 14 rotates at 2n revolutions per second, which is twice the speed of the stator 16 at n revolutions per second. The rotor is thus rotating n revolutions per second relative to the stator. The rotations effectively eliminate any counter-rotation of the rotor. In other words, the rotor no longer moves in a circle around the stator axis. The rotor axis remains stationary at a fixed, parallel distance E from the stator axis.

At each cross-section, the rotor oscillates sinusoidally between the two extremes of the stator, i.e., between 2E and −2E, leaving empty spaces on each side of the rotor. (When the rotor cross-section is at either extreme, there is only one empty space. Otherwise there are two.) The empty spaces form sealed pockets, i.e., cavities, which transport the blood along a straight forward path through the pump. The movement of the rotor and stator is described mathematically in commonly owned U.S. Pat. No. 6,361,292.

As described in U.S. Pat. No. 6,361,292, the advantage of this mode of operation is that the blood travels on a straight path through the pump, rather than along a helical path. There is no radially directed blood flow. As a result, there is less damage to the blood cells because there is no centrifugal force driving the blood against the walls of the pump chamber. There is also a decreased probability that thrombus (blood-clotting) will occur inside the pump because the blood is pushed along gently along a straight path.

The pump rotor 14 and pump stator 16 is driven by a motor 17. In a preferred embodiment, the motor 17 operates by generating a rotating electromagnetic field. This can be done using a three-phase current, e.g., with a sinusoidal waveform (alternating current) or, more probably, with a square waveform (direct current). The pump 10 preferably utilizes a segmented motor design for driving the pump. A segmented motor design is preferable in axial flow VADs to compensate for the reactive force on the pump rotor and pump stator as they carry blood through the pump. With a segmented motor design, each segment of the motor stator generates an electromagnetic force operating on the corresponding segment of the motor rotor. Now when reactive force pushes the motor rotor backward, the electromagnetic field of each segment operates to pull the motor rotor forward, back into alignment, with much greater aggregate force.

Returning to FIG. 1, the motor 17 includes a segmented motor stator 18 contained between an inner pump housing wall 20 and an outer pump housing wall 22. Thus, the motor stator 18 is outside the flow of blood. (Other components of the invention, that come into contact with blood, are constructed of materials that are blood compatible.) The motor stator 18 is comprised of motor stator windings 24 and multiple segments of motor stator laminations 26. The motor stator windings 24 can be connected to electrical input wires (not shown) to connect the pump to an external electrical source.

The motor 17 further includes a segmented motor rotor 32 rotatably secured to the inside surface of the inner pump housing wall 20 by motor rotor bearings 34. The motor rotor 32 includes multiple lamination segments 36 and an integrated outer sleeve 38. The pump stator 16 is bonded to or otherwise integrated with the motor rotor 32. Thus, the pump stator 16 is driven together with the motor rotor 32 by the motor stator 18. (When "stator" and "rotor" are used alone, they refer to the pump stator and pump rotor, respectively. The terms "motor stator" and "motor rotor" are used to refer to the motor stator and motor rotor.)

In most motors, the stator windings are connected in series. As a result, if the motor rotor is displaced radially, the magnetic field in the direction of displacement is stronger, tending to pull the motor rotor further in that direction. Consequently there is increased stress on the motor rotor bearings, which, in this case, could cause damage to blood cells. Therefore, in the preferred embodiment, the motor stator windings 24 are connected in parallel on opposite sides, with the result that the magnetic field does not tend to further displace the motor rotor 32 if it is displaced slightly radially.

The motor rotor 32 is preferably that of a squirrel cage induction motor. Other motor construction possibilities may also be used. Various motor designs are well-known to those of skill in the art, and the use of different motor designs to drive the pump of this invention is envisioned to be within the scope of this invention.

The pump rotor 14 includes an axial rotor shaft 15 supported on opposite ends by rotor bearings 28, each of which is secured to the pump housing 12 by at least one rotor bearing support 30. Unlike the pump disclosed in commonly owned U.S. Pat. No. 6,361,292, the pump rotor 14 of the present invention is directly driven by the pump motor 17. This is achieved by providing the pump 10 with a direct drive means 39 for rotating the pump rotor 14. As will be discussed below, in the preferred embodiment, the direct drive means 39 is in the form of a cooperating gear arrangement connected between the motor rotor 32 and the axial shaft 15 of the pump rotor 14. However, it is conceivable that other direct drive means can be utilized. For example, the direct drive means may take the form of a solid mechanical link between the motor rotor and the axial shaft of the pump rotor. Alternatively, the direct drive means may be a pulley or belt connecting the axial shaft of the pump rotor to the motor rotor. Additionally, the direct drive means may be a separate motor connected to the axial shaft of the pump rotor adjacent the rotor bearings for driving the rotor independently. It will be appreciated by those skilled in the art that the direct drive means can be any suitable structure coupled to the pump rotor shaft to directly drive the pump rotor.

Figure 2:
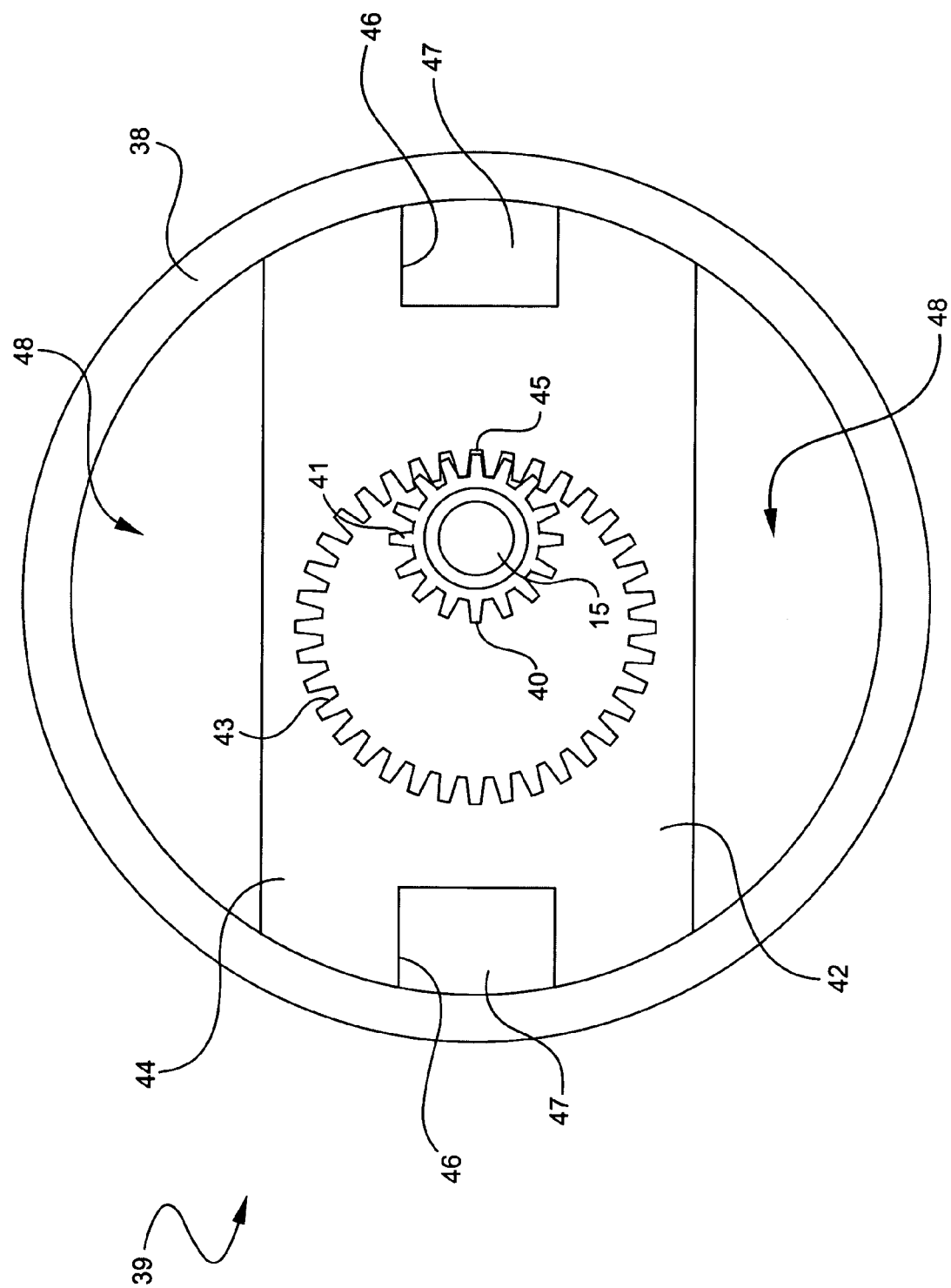
FIG. 2 is an end view of the direct drive means of the pump shown in FIG. 1 taken along the line 2—2.

As mentioned above, in a preferred embodiment, the direct drive means includes a cooperating gear arrangement connecting the axial shaft 15 of the pump rotor 14 to the motor rotor 32. As further illustrated in FIG. 2, the cooperating gear arrangement 39 includes a pinion gear 40 and a drive element 42, which is preferably in the form of a ring gear. The pinion gear 40 has external teeth 41 and is axially fixed to at least one end of the pump rotor shaft 15. (FIG. 1 shows a pinion gear 40 fixed at both ends of the rotor shaft 15.) The ring gear 42 has internal teeth 43 formed on a gear plate 44. The internal gear teeth 43 of the ring gear 42 engages the external gear teeth 41 of the pinion gear 40 in the vicinity of an intersection point 45 therebetween and thereby pushes the pinion gear to rotate. The pinion gear 40 includes m*n external teeth 41, while the ring gear 42 includes m*(n+1) internal gear teeth 43, wherein m and n are integers. In a preferred embodiment, n−1 so that there are twice as many internal teeth 43 of the ring gear 42 as there are external teeth 41 of the pinion gear 40 and, consequently, the pump rotor shaft 15 rotates twice as fast as the motor rotor-pump stator unit.

The motor rotor-pump stator unit is preferably connected to the ring gear plate 44 via the motor rotor outer sleeve 38 through a key and slot arrangement whereby, for example, slots 46 are formed on the gear plate which engage keys 47 fixed to the sleeve 38. The key and slot arrangement holds the gear plate 44 at a 90 degree angle with respect to the pump stator opening and allows the ring gear drive element 42 to slide freely in the axial direction while rotating with the motor rotor-pump stator unit as a whole.

The gear plate 44 of the drive element 42 is also designed to define openings 48 between the gear plate and the motor rotor outer sleeve 38 to allow blood to flow freely past the ring gear drive element. The openings 48 are preferably aligned with the pump stator 16 and the inlet 11 and/or the outlet 13 of the pump housing 12 so as to provide an inlet and/or outlet opening for blood flow through the pump 10 when the cavity 48 defined by the pump rotor 14 and pump stator 16 is opened at an end of the pump housing, as shown in FIG. 1.

Figure 3:
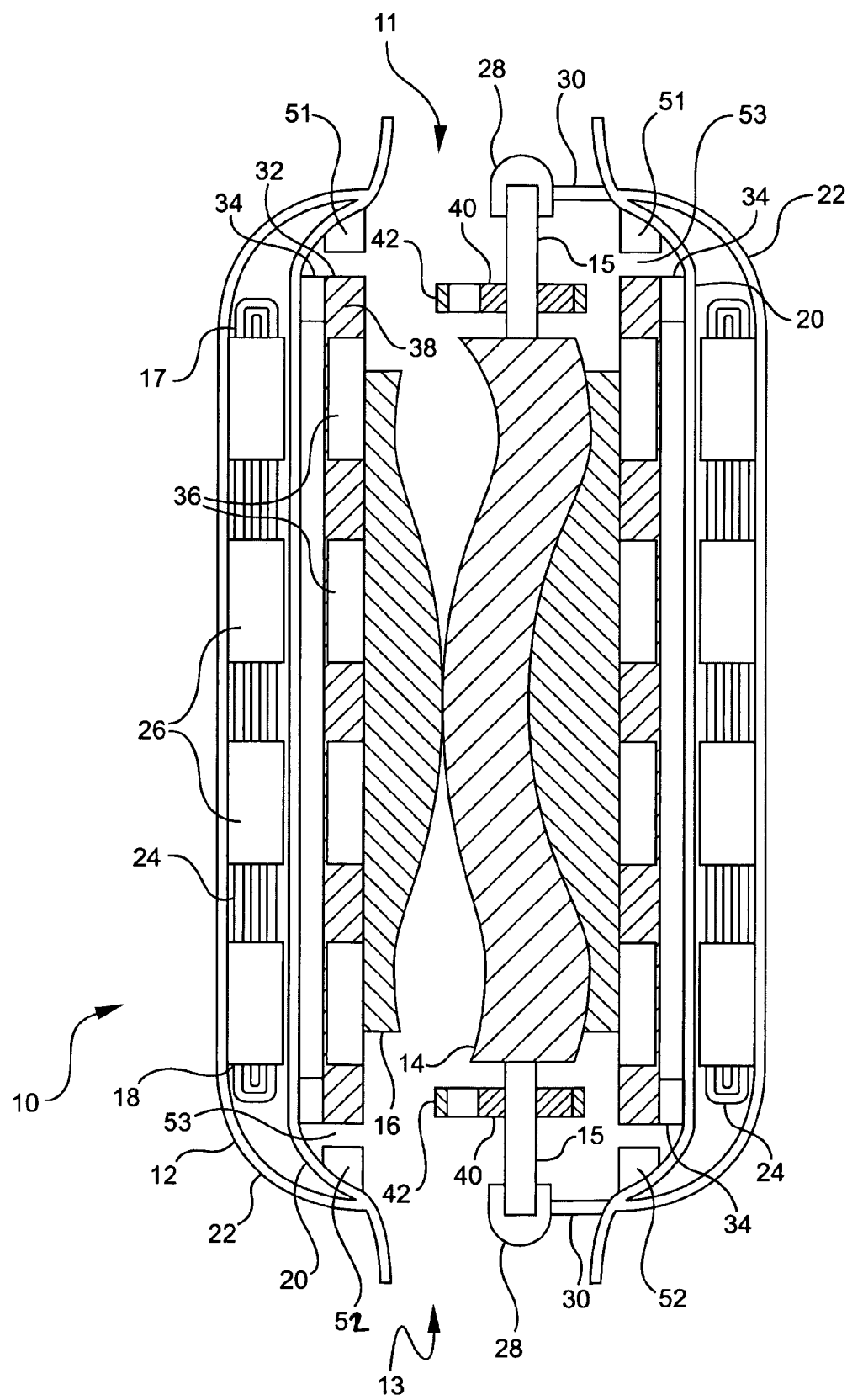
FIG. 3 shows a longitudinal cross-section view of the pump shown in FIG. 1 mounted in a vertical orientation for reducing gravitational friction loss.

In the preferred embodiment, the pump 10 is mounted vertically, as shown in FIG. 3, to minimize energy and frictional loss due to earth's gravity. In this preferred embodiment, the pump outlet 13 faces downwardly and there is little frictional loss in the bearings 34 since the bearings are now tangential to the direction of the weight of the pump. Under normal operating conditions, the weight is approximately equal and opposite to the static force of the pump output pressure. The difference between the two is within the range of the centering force between the motor stator segments 26 and the rotor segments 36. Thus, under normal operating conditions, the motor rotor-pump stator unit is "floating" vertically.

Various possible arrangements can be made such that the motor rotor-pump stator movement is limited well within the centering force range. For example, in a preferred embodiment, the pump is further provided with motion limiters 51 and 52 positioned at opposite ends of the motor rotor support sleeve 38 that limit the vertical movement of the motor rotor.

The motion limiters 51 and 52 are attached to the inner shell 20 and define a gap 53 between the motion limiters and the motor rotor. The gap 53 is approximately equal to the air gap between the motor rotor and the motor stator. In this manner, the motor rotor is allowed a vertical movement up or down equal to the width of the gap 53, while the centering force of the segmented motor keeps the motor rotor essentially floating.

In operation, the motor stator 18 drives the motor rotor 32 thereby rotating both the pump stator 16 and the internal gear drive element 42 fixed to the motor stator sleeve 38. The rotating internal gear drive element 42 directly drives the pump rotor 14 through its rotational cycle whereby the cavity 48 defined between the pump rotor and the pump stator progresses from one end of the pump housing to the other. As mentioned above, when the cavity 48 is open to the inlet 11 or outlet 13 of the pump 10, the openings 48 of the internal gear drive 42 allows free fluid flow past the internal gear drive, as shown in FIG. 1.

The present invention provides a speed doubling gear drive for directly driving the pump rotor without depending on the contour interaction between the pumping elements for rotating the pump rotor. Thus, by providing a direct gear drive, as opposed to having the pump stator alone drive the pump rotor, any problems with friction between the pump rotor and pump stator are minimized. Additionally, manufacturing tolerances between the pump rotor and pump stator can be reduced thereby reducing manufacturing costs of the pump.

It is conceivable that the present invention can utilize alternative progressive cavity pump geometries, such as those disclosed in U.S. Pat. No. 1,892,217. To accommodate alternative multi-lobe geometries, for example, the integers m and n, representing the number of external teeth 41 of the pinion gear 40 and internal teeth 43 of the ring gear 42, can be varied as required.

While there has been described what is presently believed to be the preferred embodiments of the invention, those skilled in the art will realize that various changes and modifications may be made to the invention without departing from the spirit of the invention. Accordingly, it is intended to claim all such changes and modifications as fall within the scope of the invention.

What is claimed is:

1. An axial flow blood pump comprising:
    a pump housing having an inlet and an outlet;
    a pump stator contained within said pump housing;
    a pump rotor rotatably disposed within said pump stator, said pump rotor including an axial shaft;
    a motor including a motor rotor contained within said pump housing, said motor rotating said motor rotor; and
    a direct drive means coupled to said axial shaft of said pump rotor for rotating said pump rotor,
    wherein said rotation of said pump rotor within said pump stator forms a plurality of cavities, said cavities carrying blood forward through said pump housing from said inlet to said outlet as said motor drives said direct drive means.

2. An axial flow blood pump as defined in claim 1, wherein said cavities progress in a straight line path through the pump.

3. An axial flow blood pump as defined in claim 1, wherein said pump stator is connected to said motor rotor for rotation therewith.

4. An axial flow blood pump as defined in claim 1, wherein said direct drive means is coupled between said motor rotor and said pump rotor axial shaft for rotating said pump rotor.

5. An axial flow blood pump as defined in claim 4, wherein said direct drive means comprises a gear fixed to said axial shaft of said pump rotor, said gear including a plurality of external teeth, and a drive element connected to said motor rotor, said drive element including a plurality of internal teeth engaging said external teeth of said pump rotor shaft gear.

6. An axial flow blood pump as defined in claim 5, wherein said drive element is connected with said motor rotor by a key and slot arrangement.

7. An axial flow blood pump as defined in claim 5, wherein said rotor shaft gear includes m*n external teeth and said drive element includes m*(n+1) internal teeth, wherein m and n are integers.

8. An axial flow blood pump as defined in claim 5, wherein said drive element includes twice as many internal teeth as there are external teeth of said pump rotor shaft gear so that said pump rotor is driven approximately twice as fast as said motor rotor.

9. An axial flow blood pump as defined in claim 5, wherein said drive element defines an opening for allowing blood flow past said drive element.

10. An axial flow blood pump as defined in claim 9, wherein said opening defined by said drive element is aligned with an open cavity formed between said pump shaft and said pump rotor.

11. An axial flow blood pump as defined in claim 1, wherein said motor further includes a motor stator for rotating said motor rotor, said motor stator having at least one pair of windings, said pair of windings being arranged on opposite sides of said motor stator and being connected in parallel to reduce unbalanced magnetic forces.

12. An axial flow blood pump as defined in claim 11, wherein said motor stator is contained between an inner pump housing wall and an outer pump housing wall.

13. An axial flow blood pump as defined in claim 11, wherein said motor stator and said motor rotor comprise longitudinally spaced segments.

14. An axial flow blood pump as defined in claim 13, wherein said motor rotor further comprises an outer sleeve for supporting said motor rotor segments, said drive element being connected to said outer sleeve.

15. An axial flow blood pump as defined in claim 1, wherein the axial flow blood pump is mounted vertically with said outlet facing downward.

16. An axial flow blood pump as defined in claim 15, further comprising a motion limiter for limiting vertical movement of said motor rotor.

17. A method for pumping blood through an axial flow pump including an inlet and an outlet, the method comprising the steps of:

directly rotating a pump rotor rotatably mounted within a pump stator of said pump with a motor of said pump thereby forming a plurality of moving cavities between said pump rotor and said pump stator; and carrying blood from said inlet to said outlet via said moving cavities.

wherein said motor includes a motor rotor and said pump rotor is directly rotated by a direct drive means coupling said motor rotor and an axial shaft of said pump rotor.

18. A method for pumping blood as defined in claim 17, wherein said direct drive means comprises a gear fixed to said axial shaft of said pump rotor, said gear including a plurality of external teeth, and a drive element connected to said motor rotor, said drive element including a plurality of internal teeth engaging said external teeth of said pump rotor shaft gear.

19. A method for pumping blood as defined in claim 17, wherein said pump rotor is driven approximately twice as fast as said motor rotor.

20. A method for pumping blood as defined in claim 17, wherein said moving cavities progress in a straight line path though the pump.

21. A method for pumping blood as defined in claim 17, further comprising the step of rotating said pump stator with said motor.

* * * * *